United States Patent
Grassi

[19]

[11] Patent Number: 5,944,676
[45] Date of Patent: Aug. 31, 1999

[54] BIOMEDICAL APPARATUS PARTICULARLY FOR DETECTING AND EVALUATING THE POSTURE OF THE REAR PART OF THE FEET

[75] Inventor: Silvano Grassi, Montebelluna, Italy

[73] Assignee: Sponsor S.r.l., Biadene Di Montebelluna, Italy

[21] Appl. No.: 08/927,530

[22] Filed: Sep. 11, 1997

[30] Foreign Application Priority Data

Sep. 13, 1996 [IT] Italy .................................. PD96A0224

[51] Int. Cl.$^6$ .............................. A61F 5/00; A61B 5/103
[52] U.S. Cl. .............................................. 602/23; 600/592
[58] Field of Search ................................. 602/23, 27–29; 128/882; 5/601, 624; 264/222, 223; 73/172; 378/180; 12/146 M, 142 N; 33/5; 600/592, 595

[56] References Cited

U.S. PATENT DOCUMENTS

| | | |
|---|---|---|
| 3,358,373 | 12/1967 | Martin .................................. 600/592 X |
| 3,521,876 | 7/1970 | Smith ....................................... 378/180 |
| 3,639,764 | 2/1972 | Olson et al. ............................. 378/180 |
| 4,062,355 | 12/1977 | Kaye . |
| 4,323,080 | 4/1982 | Melhart ............................... 128/882 X |
| 4,534,365 | 8/1985 | Bonetta et al. ........................... 73/172 |
| 4,827,496 | 5/1989 | Cheney .................................... 378/180 |
| 4,917,105 | 4/1990 | Tiitola et al. . |
| 5,267,949 | 12/1993 | De La Torre et al. ................ 602/23 X |
| 5,522,792 | 6/1996 | Bassett et al. ............................ 602/19 |

FOREIGN PATENT DOCUMENTS

| | | |
|---|---|---|
| 2 254 926 | 10/1992 | United Kingdom . |
| 94 20020 | 9/1994 | WIPO . |

*Primary Examiner*—Richard J. Apley
*Assistant Examiner*—Denise Pothier
*Attorney, Agent, or Firm*—Guido Modiano; Albert Josif

[57] ABSTRACT

A biomedical apparatus, particularly for detecting and evaluating the posture of the rear part of the feet (heels). The apparatus comprises a resting base provided with a flat upper surface on which, in the operating configuration, the feet of the patient being evaluated rest, and on which two removable reference heel units for the heel region of the feet are conveniently associated, so as to provide positioning of the feet. The surface has reference graduations in order to measure the gait angle or walking angle of the foot. The apparatus comprises a slider which is slidingly coupled to the base and is suitable to support and move a camera along a preset circular arc located to the rear of the heels of the patient, at a preset focal distance. The camera can be moved so as to photographically detect the resting of the heels on the ground along the median lines of the corresponding feet; the apparatus further comprises device for the comparative evaluation of the photographs taken by the camera and for calculating the thickness of a corrective wedge required to straighten a foot having a postural defect.

10 Claims, 3 Drawing Sheets

/ 34

| | 4° | 6° | 8° | 10° | 12° | 14° | 16° | 18° |
|---|---|---|---|---|---|---|---|---|
| 35-36 | 2.4 | 3.6 | 4.8 | 6 | 7.2 | 8.4 | 9.6 | 10.8 |
| 37-38 | 2.6 | 3.9 | 5.2 | 6.5 | 7.8 | 9.1 | 10.4 | 11.7 |
| 39-41 | 2.8 | 4.2 | 5.6 | 7 | 8.4 | 9.8 | 11.2 | 12.6 |
| 42-44 | 3 | 4.5 | 6 | 7.5 | 9 | 10.5 | 12 | 13.5 |
| 45-47 | 3.2 | 4.8 | 6.4 | 8 | 9.6 | 11.2 | 12.8 | 14.4 |
| 48-51 | 3.6 | 5.4 | 7.2 | 9 | 10.8 | 12.6 | 14.4 | 16.2 |

Fig. 5

BIOMEDICAL APPARATUS PARTICULARLY FOR DETECTING AND EVALUATING THE POSTURE OF THE REAR PART OF THE FEET

BACKGROUND OF THE INVENTION

The present invention relates to a biomedical apparatus particularly for detecting and evaluating the posture of the rear part of the feet (heels).

It is known that the presence of postural defects in a person's normal way of resting his feet on the ground can lead to particularly unpleasant consequences for the legs and back.

Merely by way of example, mention can be made of lumbar pains, gradual variation of skeletal geometry with a tendency to gradually lose correct and healthy posture, articular pains, etcetera.

In order to eliminate defects in the resting of the feet on the ground, corrective wedges are usually used which are contoured with variable thicknesses and shapes and are meant to be applied under the soles of shoes or to orthopedic plantar inserts.

Devices are currently available which include a base with a flat upper surface and by an abutment heel unit, on which the feet of the patient being evaluated rest in the operating position.

In particular on the, upper surface locator graduations are provided which allow the operator to detect the gait angle or walking angle of both feet.

SUMMARY OF THE INVENTION

The aim of the present invention is to provide a biomedical apparatus particularly for detecting and evaluating the posture of the rear part of the foot which allows precise detection of defects and visibly and automatically provides safe and durable references which allow evaluation even when the patient is no longer subjected to direct detection.

Within this aim, an object of the present invention is to provide an apparatus which allows quick and accurate detection without however entailing any particular inconvenience for the patient and for the operator.

Another object of the present invention is to provide an apparatus which is particularly flexible in relation to the various morphological configurations of the feet of patients.

Another object of the present invention is to provide an apparatus which can optionally be integrated with other devices for a more general and significant evaluation of the overall posture of the patient.

This aim, these objects and others which will become apparent hereinafter are achieved by a biomedical apparatus, particularly for detecting and evaluating the posture of the rear part of the foot, of the kind comprising a resting base provided with a flat upper surface on which, in an operating configuration, the feet of a patient being evaluated at rest, and on which two removable reference heel units for the heel region of the feet are conveniently associated, so as to provide positioning of said feet, said surface having reference graduations in order to measure a gait angle or walking angle of the foot, said apparatus comprising a slider which is slidingly coupled to said base, said slider being suitable to support and move a camera along a preset circular arc located to the rear of the heels of the patient, at a preset focal distance, said camera being movable so as to photographically detect the resting of the heels on the ground along median lines of the corresponding feet, said apparatus further including means for the comparative evaluation of the photographs taken by said camera and for calculating the thickness of a corrective wedge required to straighten a foot having a postural defect.

BRIEF DESCRIPTION OF THE DRAWINGS

Further characteristics and advantages of the present invention will become apparent from the following detailed description of an embodiment thereof, illustrated only by way of non-limitative example in the accompanying drawings, wherein:

FIG. 5 shows an evaluation table which is a component of the apparatus of FIG. 1.

DESCRIPTION OF THE PREFERRED EMBODIMENTS

Figure 1:
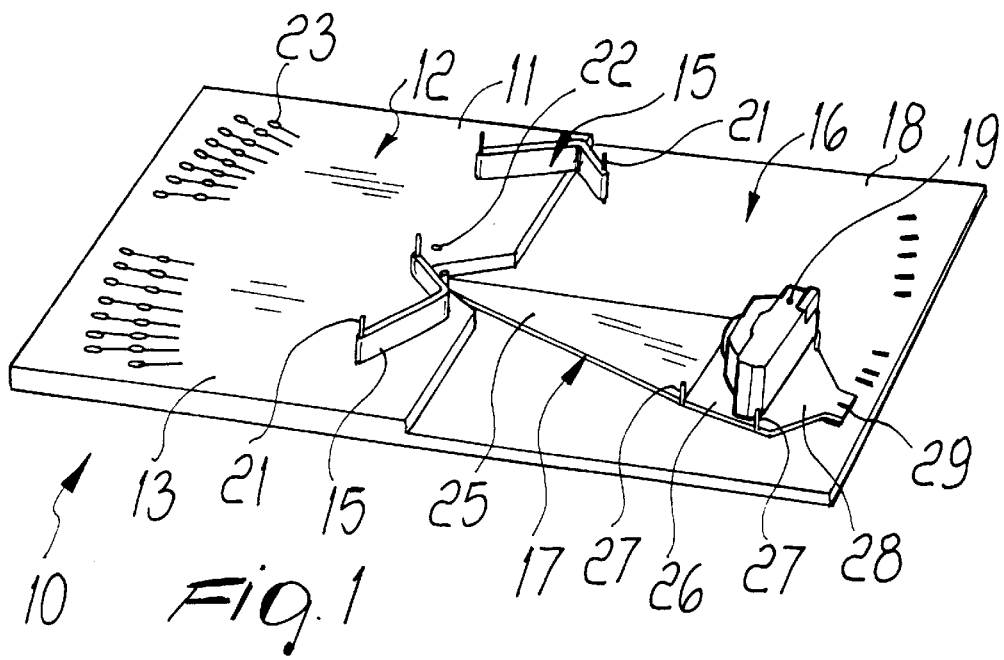
FIG. 1 is a perspective view of a biomedical apparatus according to the invention.
Figure 2:
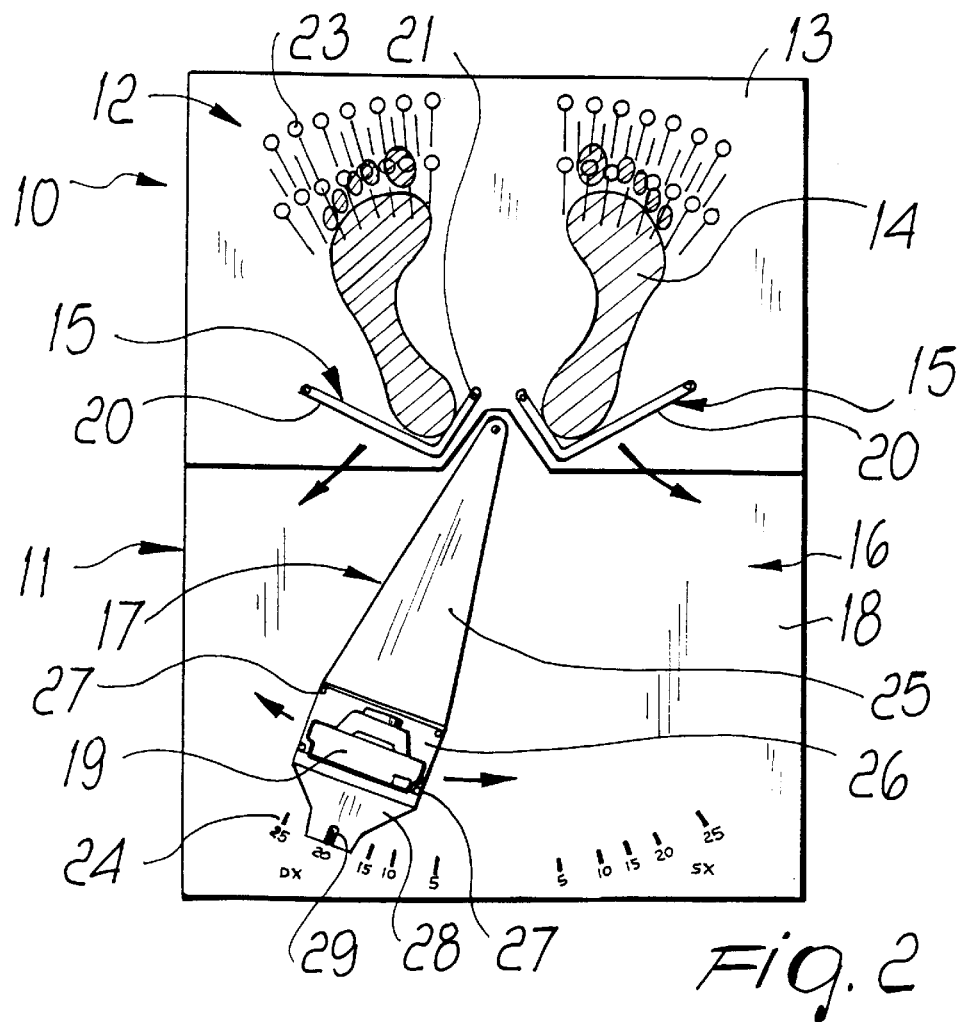
FIG. 2 is a plan view of the apparatus of FIG. 1.
Figure 3:
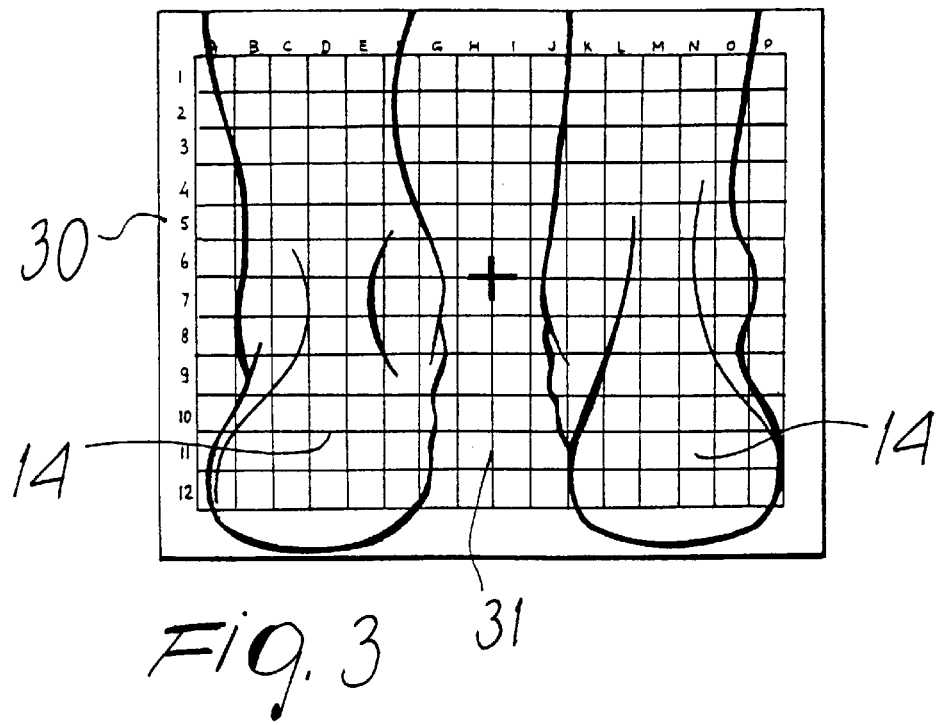
FIG. 3 is a view of a particular component of the apparatus of FIG. 1, shown in its operating configuration.
Figure 4:
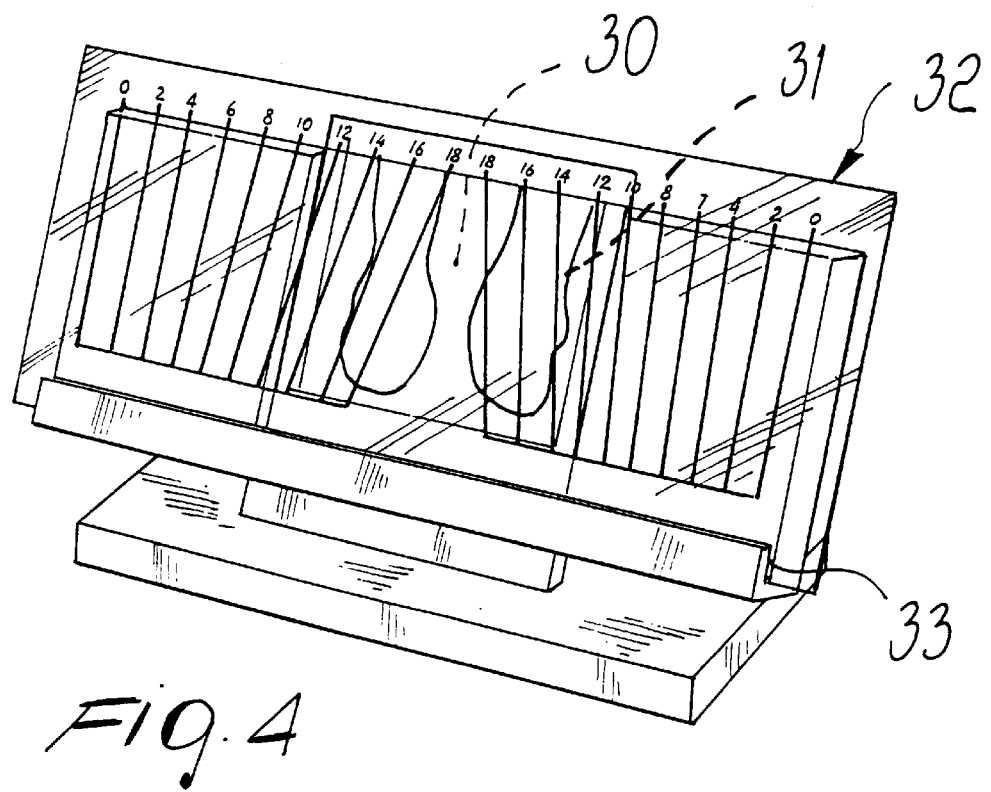
FIG. 4 is a perspective view of another component of the apparatus of FIG. 1.

With particular reference to FIGS. 1 to 4, a biomedical apparatus, particularly for detecting and evaluating the posture of the rear part of the foot, according to the present invention, is generally designated by the reference numeral 10.

The apparatus 10 comprises a resting base 11, which in this case has two regions.

A first region, designated by the reference numeral 12, has a flat upper surface 13 on which the feet, designated by the reference numeral 14, of the patient being evaluated rest in the operating configuration; two heel units 15 for positioning the heel region of the feet 14, described in greater detail hereinafter and suitable to provide uniform positioning of the feet, are conveniently associated with the flat surface.

A second region, designated by the reference numeral 16 and located at a lower level than the first region 12 in the normal operating configuration, slidingly supports a slider generally designated by the reference numeral 17.

More specifically, the slider 17 is pivoted to the upper surface 18 of the second region 16, at a median region between the heel units 15 and therefore between the heels of the feet 14 of the patient.

The slider 17 is suitable to support and move a camera 19 along a circular arc which lies behind the heels of the patient.

The camera 19, which is preferably of the kind capable of taking two pictures side by side in the same frame, can thus photographically detect the resting of the heels on the ground along median lines of the corresponding feet 14.

This detection is possible because the heel units 15 can be removed from the detection path of the camera 19.

More specifically, each one of the heel units 15, in this case, is constituted by an L-shaped element 20 in which the concavity is directed away from the camera 19; the heel of the patient is placed in the concavity.

The outer end of the shaped element is pivoted to the upper surface 13, whilst the other end is locked by virtue of the insertion of a pin 21 associated therewith in a hole 22 which is also formed in the upper surface 13.

Accordingly, once the patient has been positioned, the shaped elements 20 can be conveniently opened out so as to avoid interfering with the detection path of the camera 19.

In particular, in this case, the first region 12 has, on its upper surface 13 reference, graduations 23 for locating the gait degree of divarication of the feet 14, whilst the upper surface 18 of the second region 16 has locator graduations 24 for locating the position of the camera 19 which correspond to the gait angle of the feet of the graduations 23.

In this case, the slider 17 comprises an elongated triangular arm 25 which is pivoted, at one corner, along the larger bisector, which is continued monolithically with a base 26, which in this case is substantially rectangular, for the camera 19, from which four reference and locking pins 27 for the camera protrude.

Moreover, the base 26 is extended further in a radial direction so as to form a tab 28 which is shaped so as to form a reference recess 29 for the locator graduation 23.

The apparatus 10 also comprises means, designated by the reference numeral 30, for the comparative evaluation of the photographs taken by the camera 19 and for calculating the thickness of a wedge required to straighten a foot which has a postural defect (talipes varus-valgus).

In this case, the evaluation means are constituted by a graduated transparent mask 31 with wires and by an alphanumeric evaluation table 34, which, starting from the gait angle of the foot, provides the value of the necessary corrective wedge, determined from geometric studies carried out in this field.

In this case, moreover, the apparatus 10 is provided with a support 32, conveniently of the book-rest type, in a downward region whereof there is provided a longitudinal seat 33 inside which the photographs taken by the camera 19 and the graduated mask can slide in order to achieve precise detection.

In practice, the detection process performed with the apparatus 10 is as follows: the patient is placed on the base 11 at the first region 12, making him rest his heels in the hollows formed by the heel units 15, with his feet in their normal position and with restraint only for the heels.

Once the patient has been positioned, the heel units 15 are opened in order to avoid interfering with photographic detection.

Then the slider that supports the camera 19 is placed in sequence at the median directrices of the feet 14 of the patient, detecting in a single photograph the ground resting conditions thereof from the rear.

The photograph taken, which shows both feet side by side, is then subjected to comparison with the aid of the grid-equipped and graduated masks, in which in particular the resting angle of the rear of the feet or heels (valgoid-varus condition) is evident.

Then, by using the alphanumeric evaluation table 34 compiled on the basis of geometric studies, it is possible to achieve, as a function of the width of the shoe of the patient in the heel region and the resting angle of the rear feet of heels, an exact determination of the thickness of the wedge to be applied.

In practice it has been observed that the present invention has achieved its intended aim and objects.

In particular, it should be noted that the apparatus according to the present invention, by comparing stable media such as photographs, automatically allows precise and effective detection without having to visually frame the foot to be photographed.

It should also be noted that the operator is assisted, in his evaluation, by particularly precise and easily readable reference data.

Attention is also drawn to the possibilities of adapting of the apparatus according to the present invention to the most disparate application requirements and to the most disparate morphological conditions of patients.

Attention is also drawn to the speed of the detection process, which does not subject the patient and the operator to the slightest discomfort.

The present invention is susceptible of numerous modifications and variations, all of which are within the scope of the inventive concept; thus, for example, the heel units can be inserted in appropriate seats formed on the upper surface of the base and can be removed after positioning the patient by simple extraction from said seats.

The materials and the dimensions may be any according to requirements.

What is claimed is:

1. A biomedical foot kit, for detecting and evaluating the posture of the rear part of the foot, comprising a resting base provided with a flat upper surface on which, in an operating configuration, the feet of a patient being evaluated rest, and on which two removable reference heel units for the heel region of the feet are connected, so as to provide positioning of said feet, said surface having reference graduations in order to measure a gait angle or walking angle of the foot, the kit further comprising a slider slidingly coupled to said base and a camera, said slider supporting and moving said camera along a preset circular arc, said heel units having a front and a rear end, the heels of the patient being located in front of the front end of each heel unit during use, said slider being slidably coupled to the base along said circular arc which is located behind the rear end of each heel unit, at a preset focal distance, said camera being movable so as to photographically detect the resting of the heels of the patient on the ground along median lines of the corresponding feet.

2. The biomedical foot kit according to claim 1, wherein the base further comprises a first resting region adapted for the feet of the patient and a second resting region on which said slider is slidingly supported.

3. The biomedical foot kit according to claim 2, wherein said second region has the reference graduations for the positioning of said camera which correspond to the gait angle of the foot along the median line of the foot.

4. The biomedical foot kit according to claim 2, wherein said slider comprises an elongated arm which is pivoted at one corner along a larger bisector and continues monolithically with a rectangular base for positioning and fixing said camera.

5. The biomedical foot kit according to claim 4, wherein said base extends monolithically from a triangular arm, so as to form a tab which is shaped so as to constitute a reference pointer for a locator graduation provided in said second region.

6. The biomedical foot kit according to claim 1, further comprising means for the comparative evaluation of the photographs taken by said camera and for calculating the thickness of a corrective wedge required to straighten a foot having a postural defect.

7. The biomedical foot kit according to claim 6, wherein said comparative evaluation means comprises a mask with numbered degrees of inclination provided with graduations.

8. The biomedical foot kit according to claim 7, further comprising a support with a seat for the sliding of lower edges of the photographs taken and of the graduated mask.

9. The biomedical foot kit according to claim 6, wherein said comparative evaluation means comprises alphanumeric evaluation tables determined from geometric studies in order to achieve, as a function of the width of the shoe of the patient in the heel region, an exact determination of the thickness of the wedge to be applied.

10. The biomedical foot kit according to claim 1, wherein said camera is of the type that takes two photographs side by side in the same frame.

\* \* \* \* \*